United States Patent
Fritz et al.

(10) Patent No.: US 7,232,408 B1
(45) Date of Patent: Jun. 19, 2007

(54) RADIATION SOURCE FOR ENDOVASCULAR RADIATION TREATMENT

(75) Inventors: Eberhard Fritz, Braunschweig (DE); Gerd Phillips, Berlin (DE)

(73) Assignee: AEA Technology QSA GmbH, Braunschweig (DE)

( * ) Notice: Subject to any disclaimer, the term of this patent is extended or adjusted under 35 U.S.C. 154(b) by 0 days.

(21) Appl. No.: 10/018,623

(22) PCT Filed: Jun. 19, 2000

(86) PCT No.: PCT/EP00/05632

§ 371 (c)(1),
(2), (4) Date: Mar. 22, 2002

(87) PCT Pub. No.: WO00/78395

PCT Pub. Date: Dec. 28, 2000

(30) Foreign Application Priority Data

Jun. 18, 1999 (EP) .................................. 99111100

(51) Int. Cl.
*A61N 5/00* (2006.01)
(52) U.S. Cl. ........................................................ 600/3
(58) Field of Classification Search ................ 600/1–8
See application file for complete search history.

(56) References Cited

U.S. PATENT DOCUMENTS

| | | | | |
|---|---|---|---|---|
| 4,584,991 A | * | 4/1986 | Tokita et al. | 600/3 |
| 5,199,939 A | | 4/1993 | Dake et al. | |
| 5,342,283 A | * | 8/1994 | Good | 600/8 |
| 5,460,592 A | * | 10/1995 | Langton et al. | 600/7 |
| 5,503,614 A | * | 4/1996 | Liprie | 600/7 |
| 5,556,389 A | * | 9/1996 | Liprie | 604/264 |
| 5,683,345 A | * | 11/1997 | Waksman et al. | 600/3 |
| 5,833,593 A | | 11/1998 | Liprie | |
| 5,857,956 A | * | 1/1999 | Liprie | 600/7 |
| 5,863,284 A | * | 1/1999 | Klein | 600/3 |
| 5,997,463 A | * | 12/1999 | Cutrer | 600/8 |

(Continued)

FOREIGN PATENT DOCUMENTS

DE 281869 2/1915

(Continued)

*Primary Examiner*—Samuel G. Gilbert
(74) *Attorney, Agent, or Firm*—Akerman Senterfit; Stephan A. Pendorf

(57) ABSTRACT

According to the invention there is provided a radiation source for use in endovascular radiation treatment which comprises one or more and preferably at least two treating elements or seeds comprising a radiation emitting element and means for containment of said radiation emitting element which radiation source is characterized in that said seeds comprised in an elongated container having at least one deflection site. There is further provided an apparatus for endovascular radiation treatment comprising an elongated catheter, optionally a guide wire and the radiation source as defined above. According to another aspect there is provided a method for endovascular radiation treatment comprising the steps of directing an elongated catheter to the selected site to be treated, introducing a radiation source as defined above into the catheter at its proximal end portion, moving said radiation source to the distal end portion of the catheter preferably by use of a transfer wire, maintaining said radiation source at that distal end portion for a predetermined period of time and retracting said radiation source to the proximal end portion of the catheter preferably by use of a transfer wire.

30 Claims, 2 Drawing Sheets

U.S. PATENT DOCUMENTS 6,179,768 B1 * 1/2001 Loffler et al. ................... 600/7
6,273,851 B1 * 8/2001 Slater et al. ................... 600/8
6,506,145 B1 * 1/2003 Bradshaw et al. ............. 600/3

FOREIGN PATENT DOCUMENTS

| EP | 0 993 843 A2 | 4/2000 |
| WO | WO 9640352 | 12/1996 |
| WO | WO 97/17104 | 5/1997 |
| WO | WO 97/18012 | 5/1997 |
| WO | WO 97/37715 | 10/1997 |
| WO | WO 98/55179 | 12/1998 |

* cited by examiner

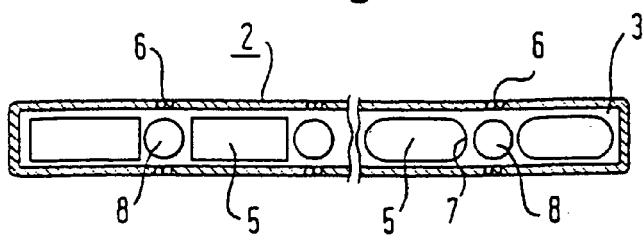
Fig. 2
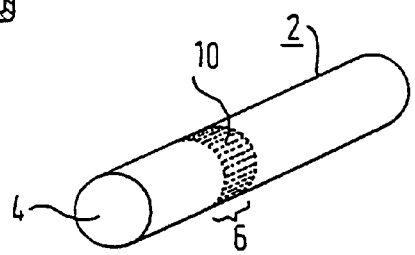
Fig. 4
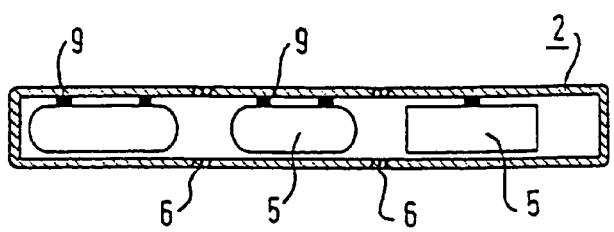
Fig. 3
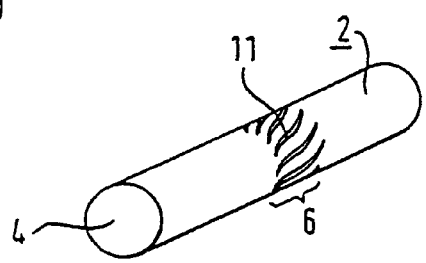
Fig. 5
Fig. 6
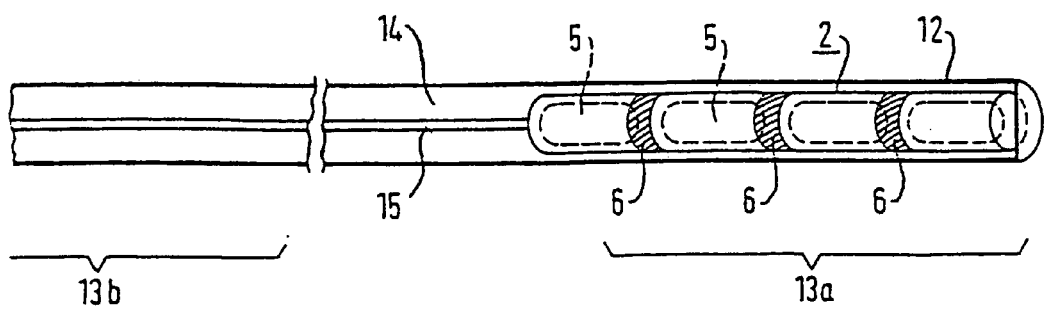

RADIATION SOURCE FOR ENDOVASCULAR RADIATION TREATMENT

The present invention relates to a radiation source for use in endovascular radiation treatment which radiation source comprises radiation emitting elements and is suitable for being delivered in a catheter to the selected site to be treated within the vascular system of a patient. The invention further relates to an apparatus for vascular radiation treatment using said radiation source as well as a method of treatment.

BACKGROUND OF THE INVENTION

Endovascular radiation treatment is the todays method of choice to prevent formation of scar tissue in a blood vessel which has been injured in various ways, for example, as trauma from surgical or diagnostic procedures. One area of the vascular system of particular concerns with respect to such injury is coronary arteries that are subjected to procedures for removing or reducing blockages due to plaque within the arteries. Partial and even complete blockage of the coronary arteries by the formation of an arteriosclerotic plaque is well known and a serious medical problem. Such blockages may be treated using arterectomy devices which mechanically remove the plaque, hot or cold lasers which vaporize the plaque, stents which hold the artery open and other devices and procedures well known in the art. The most common of them is the percutaneous transluminal coronary angioplasty, more commonly referred to as balloon angioplasty.

In this procedure a catheter having an inflatable balloon at its distal end is introduced into the coronary artery, the uninflated balloon is positioned at a stenotic site and the balloon is inflated. Inflation of the balloon disrupts and flattens the plaque against the arterial wall and stretches the arterial wall, resulting in enlargement of the intraluminal passageway and increased bloodflow. After such extension, the balloon is deflated and the balloon catheter removed.

Long term success of balloon angioplasty procedures is largely limited due to restenosis or re-closing of the intraluminal passageway through the artery by formation of scar tissue. Restenosis is experienced in approximately 30 to 50% of the patients within six months after balloon angioplasty. Apparently restenosis is to a significant extend a natural healing response to the vessel injury caused by inflation of the angioplasty balloon.

Such injury of the vessel typically initiates the bodies own natural repair and healing process. During the healing process, fibrin and platelets rapidly accumulate in the endothelium and vascular smooth muscle cells proliferate and migrate into the intima. The formation of scar tissue by smooth muscle proliferation (hyperplasia) is believed to be a major contributor to restenosis following balloon angioplasty of the coronary artery.

Prior attempts to inhibit restenosis have included the use of various light therapies, chemotherapeutical agents, stents, arterectomy devices, hot and cold lasers and so on. The most promising approach to inhibit restenosis is the use of endovascular radiation therapy, i.e. the exposure of the restenotic site to ionizing or radioactive radiation.

Although endovascular radiation therapy in general has been applied advantageously, the devices available for delivery of radiation sources and the radiation sources themselves have certain drawbacks which limit their usefulness. Typically, the devices include a catheter, which is directed by way of a guide wire inserted therein to the site of treatment. The catheter is then used to internally direct the radiation source to the site of treatment.

One typical problem encountered with the catheter and/or the radiation source is related to stiffness of the source which is mostly directly proportional to its length. Thus shorter radiation sources are typically used to allow them to follow the bends of the artery. To irradiate the entire site of the vessel to be treated a so-called "stepping-treatment" is then employed, wherein the radiation source is moved back and forth in the vessel. Since, however, exact positioning is not possible in a constantly moving vessel, irradiation is not precisely controllable in this "stepping-treatment". Thus, long sources are desirable which allow for one-step treatment of the site in its entire length.

For example, U.S. Pat. No. 5,833,593 discloses a flexible source wire which is modified at its treatment end to receive a radioactive element. A plug seals the unmodified section of the source from the lumen of the modified segment or container which contains the radioactive element. Both ends of the source wire are sealed to prevent leakage of radioactivity. The source wire is then inserted in a catheter for guiding the same to the treatment site. The modified section or container itself is rigid and is only flexibly linked to the remainder, unmodified portion of the source.

From U.S. Pat. No. 5,683,345 an apparatus and a method are known which apparatus includes an elongated flexible catheter tube having proximal and distal end portions with one or more lumina extending therebetween. One or more treating elements or seeds containing radioactive material are positionable within the first lumen and are movable between the proximal and distal end portions under the force of liquid flowing through the lumina. The radiation source used according this document consists of individual treating elements which may be joined together to form a train of treating elements by use of several length of high tempered spring wire to prevent the treating elements from becoming too spaced apart while moving through the catheter.

Other typical drawbacks encountered with prior art radiation sources and devices for delivering the same to the site to be treated are related to the duration of exposure, controllability of the radiation exposure (dosage, homogeneity of treatment), the necessity to conduct a "stepping-treatment", or difficulties in completely and controllably retracting the radiation source from the catheter and therefore the risk of undesirable exposure of both the patient and any medical personal handling the treatment device. It is the object of the invention to overcome these and other drawbacks of prior art radiation sources.

SUMMARY OF THE INVENTION

In a first aspect the invention relates to a radiation source for use in endovascular radiation treatment which comprises one or more, preferably at least two treating elements (seeds) comprising a radiation emitting element and means for containment of said radiation emitting element, wherein said seeds are comprised in an elongated container having at least one deflection site.

According to a preferred embodiment the elongated container is made from a highly flexible material such as plastics, rubber, or a memory resistant material such as a Ni—Ti-alloy or an aluminum alloy, more preferably Nitinol or Tinal alloy BB.

According to a preferred embodiment, the elongated container is a hollow cylinder or tube preferably having end caps or plugs to close the same. Preferably these end caps are rounded end caps to allow for easy movement of the container.

Preferably the one or more deflection site(s) comprise perforation patterns, preferably laser perforations of the container. These perforations may be arranged in a belt around the same. The one or more deflection site(s) may also comprise multiple helical openings in the container, which as well may be arranged in a belt around the elongated container.

Preferably the seeds comprise spherical or rounded end caps on one or both ends. They may be separated from each other by interdisposing at least one spacer, preferably in form of a sphere therebetween.

According to another embodiment the seeds are spaced from each other and fixed to the inner wall of the container, preferably by way of point welding.

In another aspect the invention relates to an apparatus for endovascular radiation treatment, comprising (1) an elongated catheter having a proximal end portion and a distal end portion, a lumen extending therebetween for receiving a radiation source, (2) optionally a guide wire and a second lumen therefore, and (3) a radiation source which comprises one or more and preferably at least two treating elements (seeds) comprising a radiation emitting element and means for containment of said radiation emitting element, wherein said seeds are comprised within an elongated container having at least one deflection site.

Preferably the apparatus comprises a x-ray fluoroscopy device for monitoring the radiation source.

In another embodiment the apparatus may comprise a magnetic means for guiding the radiation source. In this case the elongated container is preferably made from a magnetic material such as Fe or an Fe-alloy.

Preferably the apparatus may also comprise a containment vessel for storage of the elongated container and/or the individual seeds. The containment vessel can be in flow communication with the catheter lumen and/or can be a separate or separable device for separate storage and/or disposal.

In a preferred embodiment the container is linked to a transfer wire for moving the same in a catheter. Such linkage may be flexible or rigid and is preferably made at the proximal end portion of the elongated container. The transfer wire may also comprise an extension of the container itself.

In a third aspect the invention relates to a method for endovascular radiation treatment, comprising the steps of
(a) directing an elongated catheter having a proximal end portion, a distal end portion and a lumen extending therebetween for receiving a radiation source, to the selected site to be treated preferably by way of a guide wire in a separate lumen,
(b) introducing a radiation source into the catheter at its proximal end portion, which radiation source comprises one or more, preferably at least two treating elements (seeds) and—wherein said seeds are comprised within an elongated container having at least one deflection site,
(c) moving said radiation source to said distal end portion of the catheter preferably by use of a transfer wire,
(d) maintaining said radiation source at said distal end portion for a determined period of time, and
(e) retracting said radiation source to the distal end portion preferably by use of a transfer wire.

Preferably moving and/or retracting in steps of (c) and/or (e) is achieved by pushing or pulling the radiation source. According to a preferred embodiment the seeds are comprised in a magnetic elongated container and the transfer wire comprises a magnet to magnetically effect said pulling of the radiation source in steps (c) and/or (e), more preferably the transfer wire itself is magnetic.

In an alternative embodiment an external magnet field may be applied to move the radiation source comprising the seeds within a magnetic elongated container by magnetic forces.

According to another embodiment movement in step (c) is achieved by pushing and movement in step (e) is achieved by pulling the elongated container using a transfer wire linked to the container at its proximal end portion.

SHORT DESCRIPTION OF THE DRAWINGS

FIG. 2 is a schematic drawing of a radiation source according to the invention comprising spheres as spacers between the seeds to form internal joints.

FIG. 3 is a schematic drawing of a radiation source according to the invention, wherein the seeds are spaced apart from each other and are fixed to the inner wall of the container by point welding.

FIG. 4 is a schematic drawing of a radiation source according to the invention wherein the deflection site of the container is formed e.g. by laser perforations.

FIG. 5 is a schematic drawing of the container according to the present invention, wherein the deflection site is formed by helical openings in the container.

FIG. 6 is a schematic drawing of the catheter of the present invention.

In the above figures like reference numerals indicate like parts of the radiation source.

DETAILED DISCLOSURE OF THE INVENTION

Figure 1A:
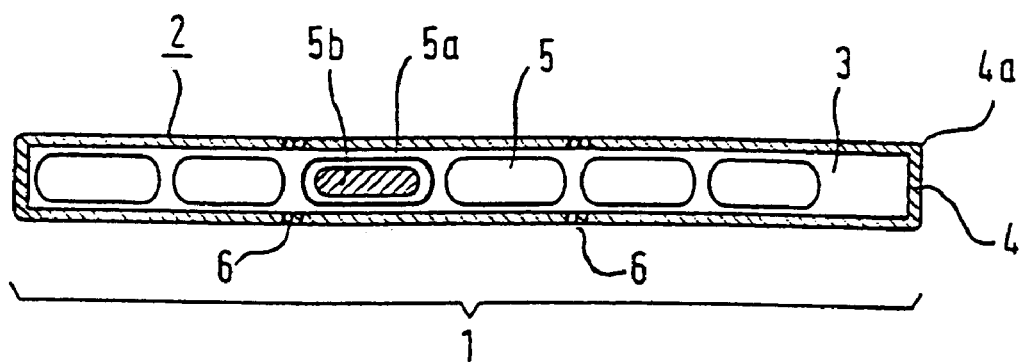
FIG. 1 is a schematic view of the radiation source according to the invention in straight (FIG. 1a) and bent (FIG. 1b) position, FIG. 1c showing various forms of the seeds to be used.

In the following the invention will more in detail be disclosed and illustrated by way of reference to accompanying drawings. Radiation in the sense of the application is to be understood as ionizing or radioactive radiation.

The radiation source for use in endovascular radiation treatment according to the invention comprises one or more, preferably at least two treating elements, so-called seeds. These seeds comprise a radiation emitting element or radiation emitting core and a means for containment of said radiation emitting element. The radiation source of the invention is characterized in that the seeds are comprised in an elongated container having at least one deflection site. Held together in the container the seeds form an elongated flexible radiation source of the desired length which length is determined by the length of the container chosen.

The expression "container" relates to any means capable of receiving and holding together the seeds, although the seeds need not necessarily be directly attached or linked to each other.

The expression "deflection site" refers to a site at which at least one deflection part of the elongated container can be made to deviate from the longitudinal axis thereof, typically by bending the same. Bending may be accomplished by some type of joint, formed internally or externally, or merely due to flexibility of the container material itself.

The expression "elongated" is used herein to indicate that the container has longitudinal axis larger than its height or depth. It is to be understood that the shape of the container can be chosen freely provided it meets the above requirement of being "elongated" and further provided its shape does not interfere with its movement in a catheter. Typically the container will thus have a circular cross-section, but may also have cross-sections of irregular, elliptic, rectangular, hexagonal, octagonal etc. form.

Preferably the container is in form of a hollow cylinder or tube preferably having end-plugs or end caps, preferably rounded (no sharp edges), at both ends to close the same. However, the container needs not necessarily be tightly closed, but may be comprised of a mesh, or a woven or non-woven material, provided this material allows to hold the seeds together within the form of the container and equally allows for providing deflection sites therein.

The container may be made from any suitable material which is sufficiently resistant against irradiation, permits transmission of radiation therethrough and allows for formation of deflection sites. Preferably the container is made from a flexible material such as plastics, thermoplastic resins, acrylics, rubber or from a memory-resistant material such as Ni—Ti-alloys e.g. Nitinol or aluminum alloys such as Tinal alloy BB. In a preferred embodiment the container is a hollow cylinder made of Nitinol and comprises rounded end caps made from the same material.

According to another embodiment the container may be made from or may comprise a metallic material which may either be a magnetic or a magnetizable material such as steel, stainless steel, Co, Ni, Fe, Mn, ferrites Ag, Pb, Co, Cr, Nb or their alloys, which magnetizable material can be magnetized by applying an external magnetic field.

The elongated container may comprise a coating layer which allows for reducing friction to improve movement of the elongated container within the catheter. This coating may be for example of teflon material or a similar low-friction material to reduce friction between the elongated container and the internal wall of the catheter in which it moves.

In case the container is made from a flexible material itself or from a mesh, a woven or non-woven web, deflection sites are constituted by appropriate choice of material of the container.

According to a preferred embodiment, the one or more deflection site(s) comprise perforation patterns, preferably laser perforations of the elongated container which are preferably arranged in a belt around the container at an appropriate site to form a deflection site. The one or more deflection site(s) may equally comprise multiple helical openings in the container. These are again arranged appropriately in a belt around the container at the suitable site.

Preferably the one or more deflection sites are arranged such that each is located exactly over the portion of the internal lumen of the container, where two end caps of seeds are opposingly faced to each other.

In a preferred embodiment the seeds comprise rounded, preferably spherical end caps on one or both sides thereof. These rounded or spherical end caps may function as internal joints. According to another embodiment the seeds are separated from each other by at least one spacer, preferably in form of a sphere preferably having about the same diameter as the seeds. This sphere may function as an internal joint. In this embodiment the seeds need not necessarily comprise rounded or spherical end caps, but may have flat end caps as well. The seeds may be spaced apart by two or more spheres interdispersed therebetween, but preferably are separated by only one sphere. The spacer itself is limited with its diameter by the internal diameter of the container and may have a smaller diameter than the seeds, provided it still sufficiently functions as an internal joint.

According to another embodiment the seeds are spaced apart from each other and are fixed to the internal wall of the elongated container to held them spaced apart and to thereby allow for providing an internal deflection site of the container. Preferably fixing of the seeds is made by point welding.

The internal diameter of the container must be sufficient to slidably receive the seeds with their means for containment typically having an outer diameter of between 0.2 and 0.8 mm. As regards the longitudinal dimension, i.e. the internal length of the lumen of the elongated container, this must be sufficient to receive the one or more, preferably at least two seeds and is preferably sufficient to receive a sufficient number of seeds to provide a radiation source of the desired length.

The internal lumen of the container may be evacuated, may comprise a gas or may comprise any suitable liquid, such as sterilized water, phosphate buffered saline, a saline solution, any inert hydrocarbon etc. provided its filling does not interfere with radiation treatment.

The outer diameter of the elongated container is as to the lower limit limited by the internal diameter thereof and is on the other hand small enough to slidably fit in a catheter and a blood vessel to be treated. Preferably such diameter is in the range of above about 0.3 to about 1 mm.

The radiation source of the present invention comprises one or more, preferably at least two treating elements or seeds. Typically the number of seeds comprised in this radiation source is chosen to cover the desired length of the vessel to be treated. Preferably the radiation source will cover a number of seeds sufficient to provide a radiation source of at least 4 mm in length, preferably 10 to 50 mm in length, more preferably 20 to 40 mm in length. The length of the elongated container is chosen appropriate thereto.

Typically the individual seeds will have a length in the range of 1.0 to 10.0 mm, more preferably 1.5 to 4.0 mm and most preferred 2.0 to 3.0 mm. Preferably the seeds are of tubular shape and have an outer diameter of the means of containment thereof in the range of between 0.2 and 1.0 mm, preferably between 0.2 and 0.8 mm.

The means for containment typically is a capsule. This capsule may be elongated, and may be a hollow cylinder or tube comprising a first and a second end plug, but may have any shape suitable for forming seeds such as spheres, ellipsoids, doughnuts, cones, flat-end-tubes, disks, cubes etc., provided it comprises a cavity for receiving and enclosing said radiation emitting element.

Preferably the means for containment is a metallic capsule which is, for example, made from a metal selected from the group comprising stainless steel, Ag, Pt, Ti, Ni, Fe, Mn, Cr, Nb, Co, Au or their alloys, including mixtures thereof. More preferably the means for containment, i.e. the seed comprises rounded or spherical end caps on one or both ends, which end caps may also form the above first and second end plug. The means for containment may also be formed from glass or plastics material such acrylics e.g. by coating a solid radiation emitting element to obtain a tight coating layer, provided it prevents leakage of radioactivity in the lumen of the catheter. It may further comprise a coating e.g. of Teflon material or a similar low-friction material to reduce friction between the treating element or seed and the inner wall of the container.

The radiation emitting element comprised in that means for containment comprises any $\alpha$-, $\beta$- and/or $\gamma$-emitting substance, preferably a pure $\beta$-particle emitter or a $\beta$- and $\gamma$-emitting substance. Typically the radiation emitting element comprises one or more radioactive materials selected from the group comprising $Cs^{137}$, $Co^{57}$, $Sr^{89}$, $Y^{90}$, $Au^{198}$, $Pd^{103}$, $Se^{75}$, $Sr^{90}$, $Ru^{106}$, $P^{32}$, $Ir^{192}$, $Re^{188}$, $W^{188}$ and $I^{125}$.

The radioactive material may be contained in a solid such as metal, glass, foil or ceramics or in a free flowing form such as a powder or liquid or is dispersed in a fluid. Neither form or state of the radioactive material is crucial, provided it allows for introducing the same in the means for containment and for secure containment.

The seeds are prepared by introducing the radiation emitting element into the means for containment and closing the same, e.g. by fixing the second end plug, e.g. by welding. The seeds may also be formed by coating an appropriately shaped ceramic radioactive core with a means for containment, e.g. by dipping the core in a coating solution, sputtering etc. The entire radiation source is then prepared by introducing the desired number of seeds into the elongated container previously prepared by known techniques and closing the same, if desired.

The amount of radioactivity is typically in the range of 0.45 to 25,000 mCi per centimeter of vessel to be treated, depending on the radiation source used. The emitted radiation should be sufficient to deliver a desired dosage of from 100 to about 10,000 rads, preferably about 700 to 5,000 rads in a about 2 to 10 minutes to the tissue to be treated.

Figure 1B:
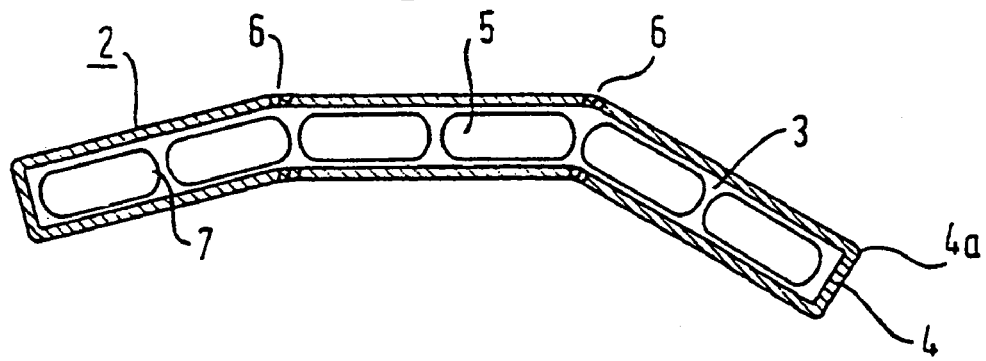

The elongated radiation source as shown in FIG. 1 comprises an elongated container (1) comprising a hollow tube (2) and flat end plugs (4) having rounded edges (4a). The internal lumen (3) of the container is adapted to receive several seeds (5) comprising a means for containment (5a) and a radiation emitting element (5b). The hollow tube of the container further comprises deflection sites (6). As can be seen from FIGS. 1 and 1a, the deflection sites (6) are located at a region of the tube where internally the spherical or rounded end caps (7) of two seeds (5) are opposingly faced to each other. Thereby, the spherical end caps function as internal joints to support bending of the deflection site(s). Further, the end caps allow for homogenous three-dimensional distribution of radiation from the seed so that bending of the radiation emitting source or the container does not result in inhomogenities of irradiation of the surrounding tissue.

Figure 1C:
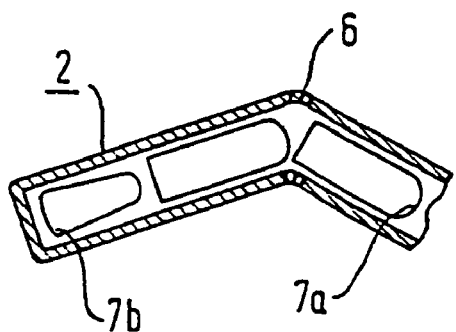

FIG. 1c shows various types of seeds with spherical (7a) or rounded (7b) end caps, which can be used in the radiation source of the invention.

According to another preferred embodiment as shown in FIG. 2, the individual seeds (5) as comprised within the container lumen (3) are spaced apart from each other by inter-disposed spheres (8). These spacers in the form of spheres need not comprise a radiation emitting element or core but may be constituted of a neutral, non-radiation emitting material.

As shown in FIG. 2 the seeds (5) may comprise spherical end caps (7), but may also comprise flat ends having rounded edges (rounded end caps), since the one or more sphere(s) interdisposed between the seeds sufficiently support bending of the deflection sites (6) already. Again the deflection site (6) is suitably located in a position surrounding the interdisposed sphere (8) to create optimal a match with the internal deflection site of the elongated container (1).

According to another preferred embodiment as shown in FIG. 3 the seeds (5) comprised in the container lumen (3) are fixed to the internal wall of the elongated container (2) by way of point welding. Fixing may occur at one or more sites on the means of the containment (9) of the seed. Preferably the deflection sites (6) of the container (2) are arranged such that they match the gaps between the seeds fixed to the internal container wall.

As can be seen from FIG. 4 and FIG. 5, according to these preferred embodiments each of the one or more deflection site(s) of the container in the respective embodiments is constituted by a belt surrounding its outer diameter of a perforation pattern (10) or e.g. helical openings (11).

The radiation source of the invention comprising an elongated container having at least one deflection site and seeds held together in this container provides a radiation source which is movable by pushing or pulling the entire container. Such movement may be accomplished by use of a transfer wire which can be mechanically and/or magnetically linked to one end of the elongated container.

The invention thereby simplifies handling of the radiation source and avoids distribution of the seeds within the catheter lumen by chance. At the same time the length of the source is not limited by its stiffness or rigidity due to the at least one deflection site provided in the container. Thus, the radiation source of the invention allows for an elongated source permitting a one-step radiation treatment of elongated segments of the vessel. Due to the one or more deflection site(s) provided in the elongated container of the radiation source of this invention, the radiation source can easily follow the bends and partitions of a blood vessel within the body to be treated.

Since the radiation source of the invention can be moved by pushing and pulling the radiation source of the invention can be used in a catheter comprising only one central lumen for receiving the source and optionally the transfer wire. Accordingly, the radiation source or its seed can be arranged in the central axis of the vessel to be treated to allow for a uniform and homogenous radiation of the surrounding tissue. This has to be considered an important aspect as radiation intensity decreases strongly with distance from the radiation source and an out of center location of the radiation source will result in unpredictable and non-controllable inhomogenities in the radiation field created therefrom. Thus, with an out of center arrangement of the radiation source inhomogeneous radiation of the surrounding tissue results. This is overcome by use of the present radiation source.

According to the present invention, there is further provided an apparatus for endovascular radiation treatment comprising (1) an elongated catheter having a proximal end portion, a distal end portion and a lumen extending therebetween for receiving a radiation source, (2) optionally a guide wire in a separate lumen and (3) a radiation source as disclosed above.

Referring to FIG. 6 the apparatus of the invention makes use of a catheter (12) which is typically made from nylon material although other plastic material may be used as well. The outer diameter of the catheter is sized according to the intended application, e.g. 5 mm or smaller for use in treating the stenotic site of a coronary artery. The inner diameter of the lumen (14) extending between the distal end portion (13a) and the proximal end portion (13b) of the catheter is correspondingly sized to receive the elongated container and is typically in the range of from about 0.3 to about 1.0 mm. The catheter may not have sufficient strength or torsional rigidity for insertion along a lengthy serpentine vascular path and may then require use of a guide wire. This guide wire is then arranged in a separate lumen having in most cases a smaller diameter than the lumen for receiving the radiation source. Typically angioplasty procedures result in a distance between the percutaneous entryport and the coronary artery of approximately 90 to 120 cm, the length of the catheter corresponding thereto. The lumen may internally have a coation for to reduce friction and/or may be filled with a suitable liquid such as mentioned above for the elongated container.

To assist in positioning the distal end portion (13a) of the catheter (12) at the desired location or site to be treated, the catheter may be advanced over a guide wire (not shown) that is pre-inserted to the desired location in the manner well known in the art. The guide wire is one commonly used in prior art and can be made from any type of metal, preferably memory-resistant metals, i.e. materials that can accept up to a 1% strain with less than a 1% permanent alteration in its original configuration. Preferred materials include nickel-titanium alloys such as Nitinol or aluminum alloys such as Tinal alloy BB. In the apparatus of the invention, a separate wire as above, the so-called transfer wire (16), is used for moving said radiation source. In the terms of the description a guide wire is used for directing the catheter, whereas a transfer wire is used for moving the radiation source.

The apparatus of the invention may further comprise a containment vessel for a storage of the radiation source and for shielding the patient to be treated and the medical personal from exposure from radiation during introduction and retraction of the catheter. The containment vessel preferably is in flow communication with the catheter, although it can be constructed as a separate and/or separable part to allow for separate storage and disposal.

The apparatus of the invention may further comprise a x-ray fluoroscopy device for monitoring the radiation source as, for example, described in U.S. Pat. No. 5,833,593. This allows for exact positioning of the radiation source, which may in this case carry a marker on one or both ends, and thus allows for precise control of the treatment site.

Finally, the apparatus of the invention may comprise a magnetic means for guiding the radiation source in case the radiation source is created from a magnetic container.

In a third aspect there is provided a method for vascular radiation treatment comprising the steps of (a) directing an elongated catheter having a proximal end portion, a distal end portion and a lumen extending therebetween for receiving a radiation source, to the selected site to be treated preferably by way of a guide wire in a separate lumen, (b) introducing a radiation source into the catheter at its proximal end portion, which radiation source comprises one or more, preferably at least two treating elements (seeds), said seeds comprising a radiation emitting element and means for containment of said radiation emitting element, and said seeds being comprised in an elongated container having at least one deflection site, (c) moving said radiation source to said distal end portion preferably by use of a transfer wire, (d) maintaining said radiation source at said distal end for a determined period of time, and (e) retracting said radiation source to the proximal end portion preferably by use of a transfer wire.

Preferably a radiation source as above is used. The steps of moving and/or retracting (c) and/or (e) can be achieved by pushing or pulling the radiation source.

More in detail, according to one preferred embodiment, movement in step (c) is achieved by pushing and said movement or retracting in step (e) is achieved by pulling said radiation source. For doing so, the radiation source may be mechanically and/or magnetically linked to a transfer wire at its proximal end. In this embodiment the radiation source is introduced in the catheter lumen at its proximal end and pushed by use of the transfer wire to its distal end. After the predetermined treatment time, the radiation source is retracted by pulling out the transfer wire from the catheter. Alternatively, the radiation source may be engaged with the transfer wire at is distal end and may be pulled by said transfer wire to the distal end of the catheter and pushed back therefrom during retracting the same.

In case of a radiation source comprising a magnetic elongated container movement of said radiation source in steps (c) and/or (e) may be achieved by applying an external magnetic field. Alternatively the transfer wire may in this case comprise a magnet to magnetically pull the radiation source in step (c) and/or (e). In a preferred embodiment the transfer wire itself is magnetic and is magnetically linked to the elongated container.

Due to the use of a catheter having a single lumen for receipt and movement of the radiation source only, the inner diameter of said lumen can be increased as compared to catheters comprising several of such lumens. Accordingly, a larger container and thus larger seeds may be used. This allows for including higher radiation dosages in each single seed. Use of a single lumen further allows for a central arrangement of the catheter and thus of the radiation source within the vessel. Thereby uniform and homogeneous radiation of the surrounding tissue is achieved. Due to the seeds being comprised in a single flexible elongated container, no gaps in the irradiated field occur and thus the radiation source needs not be moved during treatment i.e. no "stepping treatment" is required to obtain the homogeneous irradiation over the entire segment of the vessel to be treated. This further improves control of the treatment.

Of course the radiation source of the invention is not limited to use in treatment of restenotic sites, but may also be used in treatment eg. of cancer by way of irradiating the same internally.

Although being described with respect to the preferred embodiments above, this description is not to be considered limiting and the skilled worker will appreciate the possibility of several variations of the invention as defined in the appending claims, without departing from the scope of this invention.

What is claimed is:

1. A radiation source for endovascular radiation treatment comprising:
   at least two treating elements, wherein each treating element has a radiation emitting element, means for containment of said radiation emitting element, and at least one end cap;
   wherein each treating element is spaced apart from the next one,
   wherein said at least two treating elements are in an elongated metallic container comprising at least one deflection site,
   wherein the at least one deflection site is located over a portion of the internal lumen of the container where the two end caps of treating elements are opposing faced to each other.

2. The radiation source of claim 1, wherein the elongated container is a hollow cylinder.

3. The radiation source of claim 1, wherein the container is made from a highly flexible material.

4. The radiation source of claim 1, wherein the at least two treating elements comprise rounded or spherical end caps on one or both ends.

5. The radiation source of claim 1, wherein the at least two treating elements are separated from each other by at least one spacer.

6. The radiation source of claim 5, wherein said spacer is in form of a sphere.

7. The radiation source of claim 1, wherein said means for containment is a metallic capsule.

8. The radiation source of claim 1, wherein the radiation emitting element comprises any α-, β- and/or γ-emitting substance.

9. The radiation source of claim 8, wherein the radiation emitting element comprises one or more radioactive materials selected from the group consisting of $Cs^{137}$, $Co^{57}$, $Sr^{89}$, $Y^{90}$ $Au^{198}$, $Pd^{103}$, $Se^{75}$, $Sr^{90}$, $Ru^{106}$, $P^{32}$, $Ir^{192}$, $Re^{188}$, $W^{188}$ and $I^{125}$.

10. A radiation source for endovascular radiation treatment comprising:
at least two treating elements wherein each treating element is spaced apart from the next one,
wherein each treating element has a radiation emitting element, means for containment of said radiation emitting element, and at least one end cap,
wherein said at least two treating elements are in an elongated container having at least one deflection site,
wherein the at least one deflection site is located over a portion of the internal lumen of the container where the two end caps of treating elements are opposing faced to each other, and
wherein the container is made from a highly flexible material selected from the group consisting of Ni—Ti-alloy and aluminium alloy.

11. The radiation source of claim 10, wherein said flexible material is selected from the group consisting of Nitinol and Tinal alloy BB.

12. A radiation source for use in endovascular radiation treatment, the radiation source comprising:
at least one treating element having a radiation emitting element and means for containment of said radiation emitting element,
wherein said at least one treating element is in an elongated container having at least one deflection site,
wherein the at least one deflection site comprises perforation patterns.

13. The radiation source as in claim 12, wherein said patterns are laser perforations of the container.

14. A radiation source for use in endovascular radiation treatment, the radiation source comprising:
at least one treating element having a radiation emitting element and means for containment of said radiation emitting element,
wherein said at least one treating element is in an elongated container having at least one deflection site,
wherein the at least one deflection site comprises multiple helical openings in the tube.

15. A radiation source for endovascular radiation treatment comprising:
at least two treating elements each having a radiation emitting element, means for containment of said radiation emitting element, and at least one end cap,
wherein said at least two treating elements are in an elongated container having at least one deflection site,
wherein the at least two treating elements are located over a portion of the internal lumen of the container where the two end caps of treating elements are opposing faced to each other
wherein the at least two treating elements are spaced apart from each other and fixed to the inner wall of the container.

16. An apparatus for endovascular radiation treatment, the apparatus comprising:
an elongated catheter having a proximal end portion,
a distal end portion and a first lumen for receiving a radiation source, and
a radiation source which comprises at least two treating elements, wherein each treating element is spaced apart from the next one, wherein each treating element has a radiation emitting element, means for containment of said radiation emitting element, and at least one end cap,
wherein said at least two treating elements are in an elongated metallic container comprising at least one deflection site,
wherein the at least one deflection site is located over a portion of the internal lumen of the container where the two end caps of treating elements are opposing faced to each other.

17. The apparatus of claim 16, wherein the radiation source comprises a radiation emitting element comprising one or more radioactive materials selected from the group consisting of $Cs^{137}$, $Co^{57}$, $Sr^{89}$, $Y^{90}$, $Au^{198}$, $Pd^{103}$, $Se^{75}$, $Sr^{90}$, $Ru^{106}$, $P^{32}$, $Ir^{192}$, $Re^{188}$, $W^{188}$ and $I^{125}$ contained in a container made from a highly flexible material.

18. The apparatus of claim 16, further comprising a containment vessel for radiation protection.

19. The apparatus of claim 16, further comprising an x-ray fluoroscopy device.

20. The apparatus of claim 16, further comprising a guide wire.

21. The apparatus of claim 16, further comprising a second lumen.

22. An apparatus for endovascular radiation treatment, the apparatus comprising:
an elongated catheter having a proximal end portion,
a distal end portion and a first lumen for receiving a radiation source, and
a radiation source which comprises at least two treating elements each comprising a radiation emitting element and means for containment of said radiation emitting element, wherein said at least two treating elements are in an elongated container having at least one deflection site, and a magnetic means for guiding the radiation source.

23. The apparatus of claim 22, further comprising a guide wire.

24. The apparatus of claim 22, further comprising a second lumen.

25. A method for endovascular radiation treatment comprising the steps of
(a) directing an elongated catheter, having a proximal end portion, a distal end portion and a lumen extending therebetween for receiving a radiation source, to the selected site to be treated preferably by way of a guide wire in a separate lumen;
(b) introducing a radiation source into the catheter at its proximal end portion, which radiation source comprises at least two treating elements, wherein each treating element is spaced apart from the next one, wherein each treating element has a radiation emitting element, means for containment of said radiation emitting element, and at least one end cap,
wherein said at least two treating elements are in an elongated metallic container having at least one deflection site, wherein the at least one deflection site is located over a portion of the internal lumen of the container where the two end caps of treating elements are opposing faced to each other;

(c) moving said radiation source to said distal end portion preferably by way of a transfer wire;

(d) maintaining said radiation source at said distal end portion for a determined period of time; and (e) retracting said radiation source to the proximal end portion preferably by use of a transfer wire.

26. The method of claim 25, wherein moving and/or retracting in steps (c) and/or (e) is achieved by pushing or pulling the radiation source.

27. The method of claim 25, wherein said movement in step (c) is achieved by pushing and said movement in step (e) is achieved by pulling said radiation source.

28. The method of claim 25, wherein the radiation source is linked to a transfer wire at its proximal end and moving in step (c) occurs by pushing the transfer wire into the catheter and retracting in step (e) occurs by pulling the transfer wire out of the catheter.

29. The method of claim 25, wherein the radiation source comprises a radiation emitting element comprising one or more radioactive materials selected from the group consisting of $Cs^{137}$, $Co^{57}$, $Sr^{89}$, $Y^{90}$, $Au^{198}$, $Pd^{103}$, $Se^{75}$, $Sr^{90}$, $Ru^{106}$, $P^{32}$, $Ir^{192}$, $Re^{188}$, $W^{188}$ and $I^{125}$ contained in a container made from a highly flexible material.

30. A method for endovascular radiation treatment comprising the steps of (a) directing an elongated catheter, having a proximal end portion, a distal end portion and a lumen extending there between for receiving a radiation source, to the selected site to be treated preferable by way of a guide wire in a separate lumen;

(b) introducing a radiation source into the catheter at its proximal end portion, which radiation source comprises at least one treating element, wherein said at least one treating element is in an elongated container having at least one deflection site;

(c) moving said radiation source to said distal end portion preferably by way of a transfer wire;

(d) maintaining said radiation source at said distal end portion for a determined period of time; and (e) retracting said radiation source to the proximal end portion preferably by use of a transfer wire, the radiation source comprising a magnetic elongated container is used and movement in steps (c) and/or (e) is achieved by magnetically pushing and/or pulling the radiation source using a transfer wire comprising a magnet or using an external magnetic means for guiding the radiation source.

* * * * *